United States Patent [19]

Frangatos

[11] 4,267,063
[45] May 12, 1981

[54] AMINE DERIVATIVES OF DIALKYLPHOSPHONATE-ALKLMALEATE ESTER REACTION PRODUCTS AS ANTIWEAR/LOAD CARRYING ADDITIVES AND LUBRICANTS CONTAINING SAME

[75] Inventor: Gerassimos Frangatos, Haddonfield, N.J.

[73] Assignee: Mobil Oil Corporation, New York, N.Y.

[21] Appl. No.: 122,918

[22] Filed: Feb. 20, 1980

[51] Int. Cl.$^3$ ............................................. C10M 1/46
[52] U.S. Cl. ................................. 252/49.9; 252/565; 260/984
[58] Field of Search ............................. 252/49.9, 32.5

[56] References Cited

U.S. PATENT DOCUMENTS

| | | | |
|---|---|---|---|
| 3,553,131 | 1/1971 | Hepplewhite et al. | 252/49.9 X |
| 3,553,265 | 1/1971 | Maier | 252/49.9 X |
| 4,052,324 | 10/1977 | Braid | 252/49.9 X |
| 4,077,892 | 3/1978 | Frangatos | 252/49.9 |
| 4,144,180 | 3/1979 | Andress, Jr. | 252/32.5 |

*Primary Examiner*—Andrew Metz
*Attorney, Agent, or Firm*—Charles A. Huggett; Michael G. Gilman; Howard M. Flournoy

[57] ABSTRACT

Excellent load-carrying and antiwear additives are provided when reaction products of dialkylphosphonates and maleate esters are converted to amine derivatives.

8 Claims, No Drawings

AMINE DERIVATIVES OF DIALKYLPHOSPHONATE-ALKLMALEATE ESTER REACTION PRODUCTS AS ANTIWEAR/LOAD CARRYING ADDITIVES AND LUBRICANTS CONTAINING SAME

BACKGROUND OF THE INVENTION

1. Field of the Invention

This invention is directed to lubricant compositions having improved antiwear/load-carrying characteristics. More specifically this invention is directed to lubricant compositions wherein such improved characteristics are obtained by incorporating minor amounts of amine derivatives of the reaction product of a dialkylphosphonate and a maleate ester.

2. Description of Prior Art

The metal surfaces of machinery or engines operating under heavy loads wherein metal slides against metal may undergo excessive wear or corrosion. Often the lubricants used to protect the metal surfaces deteriorate under such heavy loads and as a result, do not prevent wear at the points of metal to metal contact. Consequently, the performance of the machine or engine will suffer, and in aggravated cases the machine or engine may become completely inoperative.

There have been many attempts to devise additive systems which would provide satisfactory protection, but these have not always been successful. The phosphonate derivatives of the present invention are believed capable of overcoming some of the deficiencies of prior art additives and to provide lubricating oil compositions with enhanced antiwear characteristics.

U.S. Pat. No. 2,758,971 describes a class of metal phosphonates which are disclosed as having properties which prevent breakdown of oils at high temperatures.

In U.S. Pat. No. 2,792,374 are disclosed the alkali metal salts of certain alkyl alkylphosphonic acids as defoamants in aqueous systems.

U.S. Pat. No. 2,982,727 discloses lubricating oil compositions containing certain salts of oxygen-containing esters of phosphorous. The esters are phosphonates similar to those described in U.S. Pat. No. 2,758,971.

SUMMARY OF THE INVENTION

The present invention provides lubricant compositions comprising a lubricant and an antiwear/load-carrying amount of a product prepared by reacting a maleate ester, e.g., a dialkyl maleate ester, with a dialkylphosphonate, e.g., dibutyl phosphonate, and then further reacting the resulting product with an amine, e.g., phenylenediamine.

DESCRIPTION OF SPECIFIC EMBODIMENTS

The dialkylphosphonates useful in preparing the additives of this invention will generally have from 1 to about 30 carbon atoms per alkyl group. Typical phosphonates include dimethyl phosphonate, dibutyl phosphonate, dihexyl phosphonate, dioctyl phosphonate, di-tridecyl phosphonate, di-tetradecyl catechol phosphonate, diisodecyl phosphonate, mixtures thereof and mixtures of such mono- and dialkyl phosphonates.

The amines useful in preparing the reaction products of this invention include primary and secondary alkyl amines, wherein the alkyl group contains from 1 to about 30 carbon atoms, primary, and secondary aryl amines, the aryl group containing from 6 to about 24 carbon atoms; the polyalkylene amines such as ethylene diamine, diethylene triamine, triethylene tetramine, tetraethylene pentamine, pentaethylene hexamine, nonaethylene decamine, and the like. Preferred are aryl diamines such as o, m, or p-diaminobenzene (phenylenediamine).

Maleate esters useful in the preparation of additive compounds of this invention are alkyl or di-alkyl maleate esters having from 1 to about 30 carbon atoms. Preferred are lower alkyl esters such as dibutyl maleate. Also useful are maleic anhydrides such as maleic anhydride.

Useful products can be made by reacting from 1 mole to about 4 moles of dialkylphosphonate, preferably 1 mole, with 1 mole of maleate ester and then further reacting the product thereof with 0.5 to 3 moles of the amine. The temperature of reaction may range from about 50° C. to about 250° C., preferably about 100° C. to about 200° C., depending upon the specific reactants used. Also the reaction times may vary within wide limits, e.g., from about 1 hour to about 10 hours or more depending upon reactants used and specific reaction conditions.

The lubricants which are improved by the reaction products of this invention are mineral and synthetic lubricating oils and greases therefrom. The mineral oils will be understood to include not only the paraffinic members, but also the naphthenic members. By synthetic oils are meant synthetic hydrocarbons, polyalkylene oxide oils, polyacetals, polysilicones and the like, as well as synthetic ester oils. Included among the latter type are those esters made from monohydric alcohols and polycarboxylic acids, such as 2-ethylhexylazelate and the like. Also included are those esters made from polyhydric alcohols and aliphatic monocarboxylic acids. Those of this group are especially important and in this group are found esters prepared from (1) the trimethylols, such as the ethane, propane and butane derivatives thereof and 2,2-disubstituted propane diols and (2) the pentaerythritols reacted with aliphatic monocarboxylic acids containing from about 4 to 9 carbon atoms. Mixtures of these acids may be used to prepare the esters. Preferred among the esters are those made from pentaerythritol and a mixture of $C_5$–$C_9$ acids.

As has been indicated, the reaction products disclosed herein are useful as antiwear and load carrying agents. When so used, they may be added in amounts sufficient to impart such properties to the lubricant. Generally, the useful amount will range from about 0.25% to about 10% by weight, preferably from about 0.5% to about 2%, of the product based on the weight of the total composition.

Having discussed the invention in broad and general terms, the following are offered to illustrate it. It is to be understood that the Examples are merely illustrative and are not intended to limit the scope of the invention.

EXAMPLE 1

A mixture of dibutyl phosphonate (58.2 g., 0.3 mole), xylene (100 ml.), 1-butanol (100 ml.) and Na (0.2 g.) was placed in a flask, under nitrogen. The mixture was mechanically stirred while dibutyl maleate (68.4 g., 0.3 mole) was added dropwise over a period of thirty minutes. The temperature of the reaction mixture was raised to 82° C. without external heating by the heat of the strongly exothermic reaction. The mixture was stirred for one hour after the completion of the addition of dibutyl maleate. p-Phenylenediamine (16.2 g., 0.15 mole) was then added to the mixture. The reaction mixture was subsequently heated by means of a heating oil bath. The solvents and any volatiles were allowed to distill under atmospheric pressure. The temperature of the reaction mixture was raised to 180°–185° C. and kept for three hours. Butanol was formed and distilled off. The reaction mixture was cooled to room temperature under nitrogen and heating at 180°–185° C. was then resumed for three more hours. By the end of this period no further formation or distillation of butanol or water was noted. Yield 104 grams.

EXAMPLE 2

The preparation of Example 2, including amounts of reactants, was identical to that of Example 1. However, the yield was 105 grams.

EVALUATION OF THE PRODUCTS

The product of Example 1 was tested in the 4-Ball Test using a modified 4-Ball machine. In this test, three stationary balls are placed in a lubricant cup and a lubricant containing the additive to be tested is added thereto. A fourth ball is placed on a chuck mounted on a device which can be used to spin the ball at known speeds and loads.

To a 100 cc sample of a lubricating oil comprising an 80-20 mixture, respectively, a 150" solvent paraffinic bright mineral oil (at 210° F.) and 200" solvent paraffinic neutral mineral oil (at 100° F.) was added 1 wt. % of the product of Example 2. Table 1 summarizes the results.

The product of Example 1 was also tested under the same conditions and in a synthetic ester oil. Results are summarized in Table 2.

What is claimed:

1. A lubricant composition comprising an oil of lubricating viscosity or a grease prepared therefrom and a minor antiwear/load-carrying amount of a product prepared by (a) reacting a dialkylphosphonate and an alkylmaleate ester and (b) converting the product of (a) to an amine derivative by reacting same with an amine selected from the group consisting of primary alkyl amines, secondary alkyl amines, primary aryl amines, secondary aryl amines and polyalkylene amines; wherein the molar ratio of dialkylphosphonate to alkyl maleate ester to amine varies from about 1:1:0.5 to about 4:1:3.

2. The composition of claim 1 wherein each alkyl group of the dialkylphosphonate contains from 1 to about 30 carbon atoms, the alkyl group of said alkyl maleate ester contains from 1 to about 30 carbon atoms and said amine is an aryldiamine having from about 6 to 24 carbon atoms.

3. The composition of claim 2 wherein the dialkylphosphonate is dibutylphosphonate, the maleate ester is dibutyl maleate and the arylamine is phenylenediamine.

4. The composition of claim 1 having from about 0.025 to about 10 wt. %, based on the total weight of the composition, of the antiwear/load-carrying product.

5. The composition of claim 4 having about 1 wt. % of the antiwear/load-carrying product.

6. The composition of claims 1 or 3 wherein the oil of lubricating viscosity is selected from mineral, synthetic or mixed mineral and synthetic oils.

7. The composition of claim 6 wherein the oil of lubricating viscosity is a synthetic oil.

8. The composition of claim 7 wherein the oil of lubricating viscosity is an ester prepared from pentaerythritol and a mixture of $C_5$–$C_9$ carboxylic acids.

* * * * *

TABLE 1

| Temperature | Room Temperature | | | | 200° F. | | | | 390° F. | | | |
|---|---|---|---|---|---|---|---|---|---|---|---|---|
| rpm | 500 | 1000 | 1500 | 2000 | 500 | 1000 | 1500 | 2000 | 500 | 1000 | 1500 | 2000 |
| Load, Kg | 60 | 60 | 60 | 60 | 60 | 60 | 60 | 60 | 60 | 60 | 60 | 60 |
| Time, Minutes | 30 | 30 | 30 | 30 | 30 | 30 | 30 | 30 | 30 | 30 | 30 | 30 |
| Average Scar Diam. | | | | | | | | | | | | |
| Horizontal 1 | 0.3 | 0.3 | 0.4 | 0.4 | 0.3 | 0.3 | 0.4 | 0.4 | 0.3 | 0.4 | 0.4 | 0.4 |
| 2 | 0.3 | 0.3 | 0.4 | 0.4 | 0.3 | 0.3 | 0.4 | 0.4 | 0.4 | 0.4 | 0.4 | 0.4 |
| 3 | 0.3 | 0.3 | 0.4 | 0.4 | 0.3 | 0.3 | 0.4 | 0.4 | 0.4 | 0.4 | 0.4 | 0.4 |
| Vertical 1 | 0.3 | 0.3 | 0.4 | 0.4 | 0.3 | 0.3 | 0.4 | 0.4 | 0.3 | 0.4 | 0.4 | 0.4 |
| 2 | 0.3 | 0.3 | 0.4 | 0.4 | 0.3 | 0.3 | 0.4 | 0.4 | 0.4 | 0.4 | 0.4 | 0.4 |
| 3 | 0.3 | 0.3 | 0.4 | 0.4 | 0.3 | 0.3 | 0.4 | 0.4 | 0.4 | 0.4 | 0.4 | 0.4 |
| Final Average | 0.3 | 0.3 | 0.4 | 0.4 | 0.3 | 0.3 | 0.4 | 0.4 | 0.4 | 0.4 | 0.4 | 0.4 |
| Base Stock | | | | | | | | | | | | |
| Final Average | 0.8 | 0.9 | 2.5 | 3.1 | 0.8 | 2.0 | 2.6 | 2.7 | 1.0 | 2.4 | 3.1 | 2.9 |

TABLE 2

| Temperature | Room Temperature | | | | 200° F. | | | | 390° F. | | | |
|---|---|---|---|---|---|---|---|---|---|---|---|---|
| rpm | 500 | 1000 | 1500 | 2000 | 500 | 1000 | 1500 | 2000 | 500 | 1000 | 1500 | 2000 |
| Load, Kg | 60 | 60 | 60 | 60 | 60 | 60 | 60 | 60 | 60 | 60 | 60 | 60 |
| Time, Minutes | 30 | 30 | 30 | 30 | 30 | 30 | 30 | 30 | 30 | 30 | 30 | 30 |
| Average Scar Diameter | | | | | | | | | | | | |
| Horizontal 1 | 0.3 | 0.3 | 1.3 | 1.4 | 0.3 | 0.3 | 0.4 | 1.4 | 0.5 | 1.2 | 1.4 | 1.5 |
| 2 | 0.3 | 0.3 | 1.4 | 1.4 | 0.3 | 0.3 | 0.5 | 1.4 | 0.5 | 1.2 | 1.4 | 1.5 |
| 3 | 0.3 | 0.3 | 1.3 | 1.4 | 0.3 | 0.3 | 0.5 | 1.4 | 0.5 | 1.2 | 1.4 | 1.5 |
| Vertical 1 | 0.3 | 0.3 | 1.3 | 1.4 | 0.3 | 0.3 | 0.5 | 1.4 | 0.5 | 1.2 | 1.4 | 1.5 |
| 2 | 0.3 | 0.3 | 1.4 | 1.4 | 0.3 | 0.3 | 0.5 | 1.4 | 0.5 | 1.2 | 1.5 | 1.5 |
| 3 | 0.3 | 0.3 | 1.3 | 1.4 | 0.3 | 0.3 | 0.5 | 1.4 | 0.5 | 1.2 | 1.4 | 1.5 |
| Final Average | 0.3 | 0.3 | 1.3 | 1.4 | 0.3 | 0.3 | 0.5 | 1.4 | 0.5 | 1.2 | 1.4 | 1.5 |
| Base Stock (Drew Ester) | | | | | | | | | | | | |
| Final Average | 0.8 | 1.0 | 1.1 | 1.9 | 1.0 | 1.1 | 2.4 | 2.3 | 1.1 | 1.4 | 2.0 | 2.5 |